(12) United States Patent
Bryan et al.

(10) Patent No.: US 9,480,669 B2
(45) Date of Patent: Nov. 1, 2016

(54) METHOD OF DESTROYING AND PREVENTING BACTERIAL AND FUNGAL BIOFILM BY AMINO ACID INFUSION

(71) Applicants: The Regents of the University of California, Oakland, CA (US); Thomas Benedict Bryan, Merced, CA (US)

(72) Inventors: Thomas Benedict Bryan, Merced, CA (US); Clarissa J. Nobile, Mariposa, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 14/590,002

(22) Filed: Jan. 6, 2015

(65) Prior Publication Data
US 2015/0126571 A1    May 7, 2015

(51) Int. Cl.
*A61K 31/198* (2006.01)
*A61K 31/047* (2006.01)

(52) U.S. Cl.
CPC ............ *A61K 31/198* (2013.01); *A61K 31/047* (2013.01)

(58) Field of Classification Search
CPC ..................... A61K 31/198; A61K 31/047
USPC ............................................. 514/400, 665, 738
See application file for complete search history.

(56) References Cited

U.S. PATENT DOCUMENTS

| | | | |
|---|---|---|---|
| 5,711,937 | A | 1/1998 | Nishida et al. |
| 7,906,544 | B2 | 3/2011 | Melander et al. |
| 8,241,611 | B2 | 8/2012 | Dashper et al. |
| 8,420,673 | B2 | 4/2013 | Pasteris et al. |
| 8,425,932 | B2 | 4/2013 | Wryer et al. |
| 2011/0046041 | A1 | 2/2011 | Neesham-Grenon et al. |
| 2011/0236453 | A1 | 9/2011 | Stensen et al. |
| 2012/0315260 | A1 | 12/2012 | Ivanova et al. |
| 2013/0059096 | A1 | 3/2013 | Losick et al. |
| 2013/0123319 | A1* | 5/2013 | Bryan ................. A61K 9/0019 514/400 |
| 2014/0018438 | A1* | 1/2014 | Bryan ................. A61K 31/047 514/738 |

FOREIGN PATENT DOCUMENTS

| | | | | |
|---|---|---|---|---|
| EP | 2521542 A1 | 11/2012 | | |
| WO | WO 2011085326 A1 * | 7/2011 | ........... | A61K 31/198 |

OTHER PUBLICATIONS

Rona, Zoltan, Naturally Savvy (2013), pp. 1-13.*
Ponikau et al, Mayo Clinic Proceedings 1999, vol. 74(9), pp. 1-2.*
Mahmoud Abd et al, "N-acetylcysteine Inhibits and Eradicates Candida albicans Biofilms," American J. Infectious Diseases and Microbiology, 2014, vol. 2(5), pp. 122-130.*
Helms, Steve and Miller, Alan L., "Natural Treatment of Chronic Rhinosinusitis," Alternative Medicine Review (2006), vol. 11(3), pp. 196-207.*
Intravenous Infusion of Bone Marrow in Patients Receiving Radiation and Chemotherapy, http://www.osti.gov/energycitations/product.biblio.jsp?osti_id=4331366.
Drugs & Medications—Amino Acids-E-lyte-Glycerin IV; http://www.webmd.com/drugs/drug-63311-Amino+Acids-E-lyte-Glycerin+IV.aspx?drugid=63311&drugname=Amino+Acids-E-lyte-Glycerin+IV.
Treatment of Infections Without Antibiotics, Dan Kenner, PhD, LAc., Oct. 2007, http://www.thenhf.com/old/articles/articles_594/articles_594.htm.

* cited by examiner

*Primary Examiner* — Kamal Saeed
*Assistant Examiner* — Janet L Coppins
(74) *Attorney, Agent, or Firm* — McCarter & English, LLP

(57) ABSTRACT

Disclosed is a method comprising the administration of a 3% amino acid and 3% glycerin solution for the use of prevention and disruption of bacterial biofilms. Also disclosed is method comprising the administration of L-cysteine 0.4 g per 100 ml for the prevention and destruction of fungal biofilms.

25 Claims, No Drawings

METHOD OF DESTROYING AND PREVENTING BACTERIAL AND FUNGAL BIOFILM BY AMINO ACID INFUSION

CROSS-REFERENCE TO RELATED APPLICATION

This application is related to Non-Provisional patent application Ser. No. 13/912060, filed Jun. 6, 2013, titled "A Method Of Destroying Bacterial Biofilm Using Sterile Intravenous Or Intracavernous Glycerin" and to Non-Provisional patent application Ser. No. 13/373445, filed Nov. 15, 2011, titled "Method of Treating a systemic inflammatory disorder and damaged internal tissues."

FIELD OF INVENTION

This invention pertains to the use of solutions administered in the inhibition and destruction of bacterial and fungal biofilms.

DESCRIPTION OF RELATED ART

A biofilm occurs when microbes stick to each other on a surface. These adherent microbial cells are frequently embedded within a self-producing matrix of extracellular polymeric substance. Biofilms are also referred to as slime. The polymeric conglomeration is generally composed of extracellular DNA, proteins and polysaccharides. Initially the biofilm is weak and adhesion is by van der Waals forces. Later, the microbes form cell adhesion structures such as pili in the case of bacteria or hyphae in the case of fungi. Once colonization has begun, the biofilm grows through a combination of cell division and recruitment of extracellular components.

The development of a biofilm may allow for an aggregated cell colony to be increasingly antibiotic resistant. Microbes from the biofilm can disperse which causes the spread and colonization of new surfaces. The extracellular matrix protects the microorganisms within it and facilitates communication among them through biochemical signals. Biofilms have been implicated in such problems as urinary tract infections, endocarditis, cystic fibrosis and infections of medical devices, such as prostheses and heart valves. Invariably the only recourse for treating prosthetic devices such as mechanical heart valves is to have them replaced. Biofilms are present on the removed tissue of 80% of patients undergoing surgery for chronic sinusitis.

Danish pioneers first connected biofilms with human disease in the 1980's and then with antibiotic resistant infections. They discovered that once these biofilm infections had begun they are difficult to get rid of in the body. The immune system can mop up free-floating microbes in the blood but reaching bacteria and fungi within the biofilm reservoir is difficult.

Even if an antimicrobial agent reaches a biofilm, a large portion of the microbes would be insensitive to the specific antimicrobial agent as bacteria and fungi in a biofilm typically exist in a dormant state. The dormant microbes are not vulnerable to the antimicrobial agent. Later, these dormant microbes can quickly renew the biofilm. Low oxygen concentrations in the biofilm also protects the microbes from some antimicrobial agents, which require aerobic metabolism.

According to the Center for Disease Control, 65% of treated bacterial infections develop from a biofilm. Biofilms are implicated in chronic infections. Most notable among them is *Staphylococcus aureus*, especially the methicillin resistant (MRSA) variety. Also, an estimated 13% of intensive care patients have a fungal infection likely originating from a biofilm.

SUMMARY OF INVENTION

Disclosed is a method comprising the administration of a 3% amino acid and 3% glycerin solution for the use of prevention and disruption of bacterial biofilms.

Also disclosed is method comprising the administration of L-cysteine 0.4 g per 100 ml for the prevention and destruction of fungal biofilms.

DETAILED DESCRIPTION

A 66 year old female developed cellulitis and an open ulcer on her leg. This was treated by oral antibiotics and was also treated at an outpatient wound care center. When the outpatient care was not successful she was admitted to the hospital for intravenous antibiotics. After 3 weeks there was no sign of improvement and the ulcer was enlarging. At this stage the ulcer measured 3 centimeters by 1-½ centimeters in size and there was surrounding redness suggestive of inflammation. She was then given an intravenous solution of 3% amino acids and 3% glycerin at an infusion rate of 80 cubic centimeters (cc) per hour. At the end of 48 hours there was evidence of healing in the ulcer. During these 48 hours, the patient was continued on intravenous antibiotics. After 72 hours the patient was discharged home on oral antibiotics. When she was re-examined 3 weeks later, there was no evidence of the ulcer and the surrounding inflammation that was caused by cellulitis had totally cleared. Ulcers such as this suggest that the patient had developed a bacterial biofilm that had increased resistance to antibiotics causing the antibiotics to be ineffective.

In the lab we discovered that glycerin had little effect on biofilm inhibition.

ProcalAmine® which contains the amino acids Isoleucine 0.21 g per 100 ml, Leucine 0.27 g per 100 ml, Lysine (as Lysine Acetate USP 0.31 g) 0.22 g per 100 ml, Methionine 0.16 g per 100 ml, Phenylalanine 0.17 g per 100 ml, Tryptophan 0.046 g per 100 ml, Valine 0.2 g per 100 ml, Alanine 0.21 g per 100 ml, Arginine 0.29 g per 100 ml, Histidine 0.085 g per 100 ml, Proline 0.34 g per 100 ml, Serine 0.18 g per 100 ml, Glycine 0.42 g per 100 ml, Threonine 0.12 g per 100 ml, Cysteine (as L-cysteine hydrochloride monohydrate less than 0.020 g) less than 0.014 g per 100 ml, both inhibited and destroyed bacterial and fungal biofilms.

We found that Aminosyn 10% which contained no L-cysteine and also contained Tyrosine, Aspartic Acid, and glutamic acid did not inhibit or destroy bacterial and fungal biofilms. It was not aided by the addition of L-cysteine for the bacterial biofilms, but was aided by the addition of L-cysteine for the fungal biofilms. This may indicate that tyrosine, aspartic acid, or glutamic acid may inhibit the destructive effect of one or some of the other amino acids on the bacterial biofilm.

We also discovered that L-cysteine alone at a concentration of 0.4 g per 100 ml caused inhibition and destruction of fungal biofilms, such as those formed by the predominant human fungal pathogen, *Candida albicans*. L-cysteine alone had no effect on the bacterial biofilms.

The method used was as follows:

Inhibition and Disruption Assay In Vitro

*Candida albicans* wild-type strain SN250 was incubated on YEPD plates at 30° C. at 225 rpm for 16 hrs. *Staphylococcus aureus* wild-type strain JE2 was incubated on Blood Agar plates at 37° C. for 24 hours. A single colony from the plate was inoculated in 4 mL of TSB media and incubated at 37° C. on a rotating platform for 16 hours.

Biofilms were grown as follows: For the inhibition assay, the cells were incubated in RPMI-1640 medium alone and with compounds to be tested (1% ProcalAmine® or 0.4% L-cysteine) at 37° C. at 250 rpm for *C. albicans* and statically for *S. aureus* for 90 minutes, for cell adhesion. Cells were washed with PBS solution followed by addition of RPMI-1640 alone and with compounds to be tested (1% ProcalAmine® or 0.4% L-cysteine), and further incubated at 37° C. at 250 rpm (for *C. albicans*) and statically (for *S. aureus*) for 24 hours for biofilm growth.

For the disruption assay, the biofilm was grown in RPMI-1640 alone, following the same procedure mentioned above for *C. albicans* and *S. aureus*, with no addition to media. After 24 hours, the media was aspirated and carefully replaced by RPMI-1640 alone and with treatments (1% ProcalAmine® or 0.4% L-cysteine) and further incubated at 37° C. at 250 rpm (*C. albicans*) and statically (*S. aureus*) for 24 hours.

All biofilms formed were analyzed by measuring optical density at 630 nm. Six replicates for each treatment were performed.

These same amino acids may be used in both the prevention and the treatment of biofilms in human and animal bacterial biofilms and L-cysteine may be used in the treatment and prevention of fungal biofilm in both humans and animals.

Consequently, these solutions may be used for oral and topical prevention and treatment.

In some embodiments, a 3% amino acids and 3% glycerin solution (e.g., ProcalAmine®) may be used for oral and topical prevention and treatment with a swish and swallow method, repeated as needed. In some embodiments, the 3% amino acids and 3% glycerin solution may be used as a topical method of treatment through the irrigation of a wound with the 3% amino acids and 3% glycerin solution followed by dressing the wound with a compress moistened with the 3% amino acids and 3% glycerin solution and maintained for approximately 48 hours or due to differences in wound area and depth, until satisfactory treatment.

In some embodiments, a 0.4% L-cysteine solution may be used for oral and topical prevention and treatment of *C. albicans* biofilms with a swish and swallow method, and repeated as needed. In some embodiments, a 0.4% L-cysteine solution may be used with as a topical method for the prevention and treatment of *C. albicans* biofilm infections through the irrigation of a wound with 0.4% L-cysteine solution followed by dressing the wound with a compress moistened with 0.4% L-cysteine solution and maintained for approximately 48 hours, or due to differences in wound area and depth, until satisfactory treatment.

In some embodiments, a 3% amino acids and 3% glycerin solution (e.g., ProcalAmine®) may be used for the treatment of biofilms indicated in chronic sinusitis. In some embodiments, a 0.4% L-cysteine solution may be used for the treatment of biofilms indicated in chronic sinusitis.

We claim:

1. A method of preventing formation of and/or destroying a bacterial biofilm by an amino acid infusion comprising administering a solution of 3% glycerin and a total of 3% amino acids, wherein the step of administering comprises irrigating a wound with the solution.

2. The method of claim 1, wherein the solution further comprises a total of 3% amino acids comprising Isoleucine at 0.21g per 100 ; ml, Leucine at 0.27 g per 100 ml, Lysine at 0.22 g per 100 ml, Methionine at 0.16 g per 100 ml, Phenylalanine at 0.17 g per 100 ml, Tryptophan at 0.046 g per 100 ml, Valine at 0.2 g per 100 ml, Alanine at 0.21 g per 100 ml, Arginine at 0.29 g per 100 ml, Histidine at 0.085 g per 100 ml, Proline at 0.34 g per 100 ml, Serine at 0.18 g per 100 ml, Glycine at 0.42 g per 100 ml, Threonine at 0.12 g per 100 ml, and L-cysteine at 0.014 g or less per 100 ml.

3. The method of claim 1, wherein the step of administering comprises applying a compress moistened with the solution to the wound.

4. The method of claim 3, wherein the step of applying the compress is performed for 48 hours.

5. The method of claim 1, wherein the method of administration is by irrigating a wound with the solution of 3% amino acids and 3% glycerin, and applying a compress moistened with the solution of 3% amino acids and 3% glycerin for approximately 48 hours.

6. The method of claim 1, wherein the biofilm comprises *Staphylococcus aureus*.

7. The method of claim 1, wherein the method of administration is nasal irrigation.

8. A method of treating a fungal biofilm in an animal comprising administering a solution comprising L-cysteine, tyrosine, aspartic acid, and glutamic acid.

9. The method of claim 8, wherein the step of administration is intravenously, topically, orally, or intranasally.

10. The method of claim 8, wherein solution comprises a concentration of 0.4 grams of L-cysteine per 100 mL of aqueous solution.

11. The method of claim wherein the biofilm comprises *Candida albicans*.

12. The method of claim 8, wherein the step of administering comprises exposing the biofilm to a compress moistened with the solution.

13. A method of preventing formation of a fungal biofilm in an animal comprising administering to the animal a solution comprising L-cysteine, tyrosine, aspartic acid, and glutamic acid.

14. The method of claim 13, wherein the step of administration is performed intravenously, topically, orally, or intranasally.

15. The method of claim 13, wherein solution comprises a concentration of 0.4 grams of L-cysteine per 100 mL of aqueous solution.

16. The method of claim 13, wherein the biofilm comprises *Candida albicans*.

17. The method of claim 13, wherein the step of administering comprises exposing the biofilm to a compress moistened with the solution.

18. A method of treating or preventing chronic sinusitis comprising administering to an animal subject a composition comprising 3% glycerin and 3% total amino acids in weight to volume of an aqueous solution.

19. The method of claim 18, wherein the sinusitis is caused by a bacterial cells.

20. A method of treating or preventing chronic sinusitis caused by fungal cells comprising administering to an animal subject a composition comprising L-cysteine in an aqueous solution weight to volume of an aqueous solution.

21. The method of claim 20, wherein the method comprises administering a solution of L-cysteine at concentration of 0.4 grams of L-cysteine per 100 mL weight to volume of an aqueous solution.

22. A method of treating a fungal biofilm in an animal comprising administering a solution comprising L-cysteine and one or a combination of: isoleucine, leucine, lysine, methionine, threonine, valine, alanine, arginine, histidine, proline and serine.

23. The method of claim 22, wherein the biofilm comprises *Candida albicans*.

24. A method of preventing a fungal biofilm in an animal comprising administering a solution comprising L-cysteine and one or a combination of: isoleucine, leucine, lysine, methionine, threonine, valine, alanine, arginine, histidine, proline and serine.

25. The method of claim 24, wherein the biofilm comprises *Candida albicans*.

\* \* \* \* \*